United States Patent [19]

Dusza et al.

[11] Patent Number: 4,622,401

[45] Date of Patent: Nov. 11, 1986

[54] HETEROCYCLIC SUBSTITUTED-AMINO-PYRAZOLINES

[75] Inventors: John P. Dusza, Nanuet, N.Y.; Joseph P. Joseph, Montvale, N.J.; Seymour Bernstein, New City, N.Y.

[73] Assignee: American Cyanamid Company, Stamford, Conn.

[21] Appl. No.: 651,966

[22] Filed: Sep. 19, 1984

Related U.S. Application Data

[63] Continuation-in-part of Ser. No. 628,936, Jul. 9, 1984, abandoned, which is a continuation of Ser. No. 472,397, Mar. 4, 1983, abandoned, which is a continuation-in-part of Ser. No. 282,699, Jul. 13, 1981, abandoned.

[30] Foreign Application Priority Data

| | | |
|---|---|---|
| May 26, 1982 [CA] | Canada | 403773 |
| May 28, 1982 [EP] | European Pat. Off. | 82104682.8 |
| Jul. 12, 1982 [JP] | Japan | 57-120005 |

[51] Int. Cl.$^4$ ............................................. C07D 401/04
[52] U.S. Cl. ..................................... 544/405; 546/279
[58] Field of Search ........................ 544/405; 546/279

[56] References Cited

U.S. PATENT DOCUMENTS

| | | | |
|---|---|---|---|
| 3,169,966 | 2/1965 | Schmidt et al. | 546/279 |
| 3,927,025 | 12/1975 | Korbonits et al. | 546/279 |
| 4,096,152 | 6/1978 | Möller et al. | 544/405 |
| 4,099,011 | 7/1978 | Möller et al. | 544/405 |
| 4,113,957 | 9/1978 | Möller et al. | 544/405 |

FOREIGN PATENT DOCUMENTS 0022578  1/1981  European Pat. Off. ............ 546/279

OTHER PUBLICATIONS

Robbins et al., Pathologic Basis of Disease, 3rd edition, 1984, W. B. Saunders Co., p. 55.
Yasuo et al., Chem. Abst., vol. 66, 13685g.

*Primary Examiner*—Jane T. Fan
*Attorney, Agent, or Firm*—Susan H. Rauch

[57] ABSTRACT

This invention relates to novel 3-amino-1-heteroaryl-2-pyrazolines and their $C_4$ and $C_5$ analogs, useful for meliorating the inflammation and/or the progressive joint deterioration characteristic of arthritic disease, preventing the onset of asthmatic symptoms and allergic diseases, or as analgesic, antibacterial or antifungal agents.

1 Claim, No Drawings

4,622,401

HETEROCYCLIC SUBSTITUTED-AMINO-PYRAZOLINES

CROSS REFERENCE TO RELATED APPLICATION

This application is a continuation-in-part of Ser. No. 628,936 filed July 9, 1984, now abandoned, which is a continuation of Ser. No. 472,397, filed Mar. 4, 1983, now abandoned which is a continuation-in-part of Ser. No. 282,699, filed July 13, 1981, now abandoned.

BACKGROUND OF THE INVENTION

R. Battisti, et al., U.S. Pat. No. 4,149,005 (Apr. 10, 1979) discloses compounds of the formula:

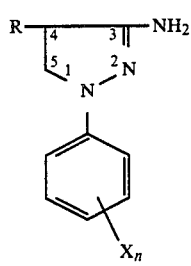

where R is H or $CH_3$, X is H, Br, Cl, alkyl, alkoxy or carboxyalkyl groups with from 1 to 4 carbon atoms or $CF_3$; and n is 1 or 2. These are disclosed as being used as intermediates in the preparation of 1-phenyl-3-aminopyrazoles as coupling components in azo dye manufacture. Related foreign patents: Ger. Offen. No. 2,727,706; French No. 2,355,834; Gr. Br. No. 1,515,500; Belgium No. 855,944; Netherland No. 7,706,760 and Japan No. 28,168.

G. A. Higgs, et al., (Wellcome Research Laboratories); Biochemical Pharmacology, 28 1959 (1979) discloses 3-amino-1-[m-(trifluoromethyl)phenyl]-2-pyrazoline (BW 755C);

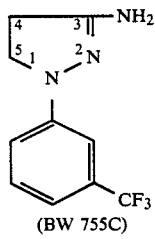
(BW 755C)

This compound is reported to have anti-inflammatory activity.

S. R. Challand et al. (The Wellcome Foundation Limited), European Patent Application No. 0022578 discloses the following compounds:

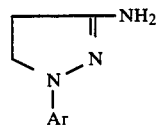

where Ar is pyridyl or phenyl, each of which may be mono- or di-substituted by trifluoromethyl, fluoro, chloro, bromo or iodo. These compounds are described as exhibiting anti-inflammatory action in mammals.

SUMMARY OF THE INVENTION

This invention relates to novel 3-amino-1-heteroaryl-2-pyrazolines and their $C_4$ and $C_5$ analogs. Such compounds are useful for meliorating inflammation, meliorating the inflammation and/or the progressive joint deterioration characteristic of arthritic disease, preventing the onset of asthmatic symptoms and allergic diseases, or as analgesic, antibacterial or antifungal agents.

DETAILED DESCRIPTION OF THE INVENTION

The instant invention concerns novel compounds of the following formula I:

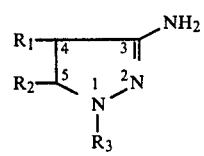

where $R_1$ and $R_2$ are the same or different and are hydrogen, lower alkyl ($C_1$-$C_4$), phenyl or halo-substituted phenyl;

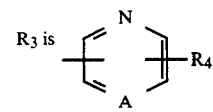

A is nitrogen or CH; and $R_4$ is hydrogen, halogen or lower alkyl ($C_1$-$C_4$); or a nontoxic pharmaceutically acceptable salt, with the proviso that when A is CH, then $R_1$ and/or $R_2$ must be phenyl or halo-substituted phenyl.

The invention further concerns a novel method of preventing the onset of asthmatic symptoms or allergic diseases in a mammal using a pharmacologically effective dose of a compound of the above formula I where $R_3$ can alternatively be benzothiazole. Additionally, the invention includes a method of meliorating inflammation by administering an effective dose of a compound of the above formula I where $R_3$ is pyrazine or benzothiazole but not pyridyl. The invention also includes methods of meliorating inflammation or the progressive joint deterioration characteristic of arthritic disease and treating pain in a mammal by the administration of an effective dose of a compound of the above formula I providing $R_3$ can only be benzothiazole. In each applicable case, $R_1$, $R_2$ and $R_4$ are as defined above.

The invention also involves a method of treating bacteria and/or fungal infections in a mammal by administering to the mammal a pharmacologically effective dose of a compound of the following formula II:

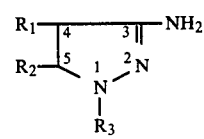

where $R_1$ and $R_2$ are the same or different and are hydrogen, lower alkyl ($C_1$-$C_4$), phenyl or halo-substituted phenyl; $R_3$ is

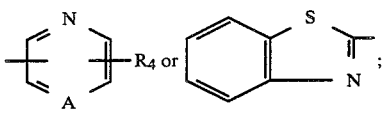

A is nitrogen or CH; $R_4$ is hydrogen, halogen or lower alkyl ($C_1$-$C_4$); and when $R_1$ and $R_2$ are both hydrogen $R_3$ can also be an alkoxy-, dihalo- or nitro, halo-substituted pyridine; or a nontoxic pharmaceutically acceptable salt.

DETAILED DESCRIPTION OF THE INVENTION

The novel compounds of the present invention are generally obtainable as white to pale yellow crystalline solids having characteristic melting points and absorption spectra. The bases are appreciably soluble in solvents such as acetone, ethanol, toluene, methylene chloride and the like but are relatively insoluble in water. The organic bases of the present invention form nontoxic acid-addition salts with variety of pharmacologically acceptable organic and inorganic salt forming reagents. Thus, acid-addition salts, formed by admixture of the organic free base with one or two equivalents of an acid, suitably in a neutral solvent, are formed with such acids as sulfuric, phosphoric, hydrochloric, hydroiodic, sulfamic, citric, lactic, fumaric, succinic, tartaric, acetic, benzoic, gluconic, ascorbic, and the like. The acid-addition salts are relatively insoluble in non-polar organic solvents such as diethyl ether, benzene, toluene, and the like but are appreciably soluble in water. For purposes of this invention, the free bases are equivalent to their nontoxic acid-addition salts.

Preparation of the novel 3-amino-1-heteroaryl-2-pyrazolines (III) of the instant invention, which exhibit the pharmaceutical activity as herein described, is accomplished by the adaptation of the procedure of Duffin, G. F. and Kendall, J. D., J. Chem. Soc. 1954: 408; in accordance with the following reaction scheme:

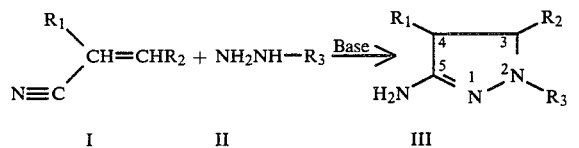

wherein $R_1$, $R_2$ and $R_3$ are as hereinabove defined. In accordance with the above reaction scheme, a heteroaryl hydrazine II (such as 2-hydrazinobenzothiazole, 2-hydrazinopyridine, 2-chloro-6-hydrazinopyridine, 3-chloro-6-hydrazinopyridine, 5-chloro-2-hydrazinopyridine, 2-chloro-6-hydrazinopyridine, etc.) is reacted with a α,β-unsaturated nitrile I such as methacrylonitrile, crotononitrile, cinnamonitrile, butylacrylonitrile, p-chlorocinnamonitrile and 4-methylcinnamonitrile or compounds such as β-ethoxypropionitrile, (which can undergo base catalyzed elimination to yield I) in a base catalyzed condensation procedure which is catalyzed with a base such as sodium ethoxide or choline hydrate in absolute ethanol. The reaction mixture is preferably refluxed for 4–16 hours then the solvent is removed in vacuo. The addition of water gives a filterable solid which is collected, dissolved and dichloromethane and passed through a short column of hydrous magnesium silicate. The column effluent is then refluxed on a steam bath with the gradual addition of hexane until crystallization is noted. Recrystallization from the same solvent pair (with or without additional treatment with hydrous magnesium silicate) or from acetone-hexane provides the desired heterocyclic substituent-aminopyrazoline compounds III of the instant invention. If the product is not soluble in dichloromethane, recrystallization may be accomplished from acetone-hexane, 95% ethanol or benzene with the omission of the hydrous magnesium silicate treatment phase.

The compounds of the instant invention have utility as pharmacological agents. They are active either as anti-inflammatory agents, analgesic agent, antibacterial and/or antifungal agents and in some cases are active in more than one of these areas. Some of the compounds of this invention are further useful in inhibiting the progression of arthritis such as rheumatoid arthritis and inhibiting the progression of joint deterioration or preventing the onset of asthma and other allergic diseases. They also find utility in the amelioration or prevention of pathological reactions such as osteoarthritis, gout, acute synovitis and psoriasis.

Representative compounds of this invention have proven to be active in vivo as anti-inflammatory agents when tested by the Carrageenin Induced Edema of The Rat Paw Test. This test is a modification of the method of Winter C. A., et al., Proc. Soc, Exp. Biol. and Med. 111:544 (1962). Compounds found to be active in this test are:

2-(3-amino-5-methyl-2-pyrazolin-1-yl)-6-chloropyrazine
2-(3-Amino-2-pyrazolin-1-yl)benzothiazole
2-(3-Amino-4-methyl-2-pyrazolin-1-yl)benzothiazole
2-(3-Amino-5-methyl-2-pyrazolin-1-yl)benzothiazole
2-(3-Amino-5-p-tolyl-2-pyrazolin-1-yl)benzothiazole Some of the compounds of the present invention also possess activity as analgesic agents. A method employed for measuring the in vivo activity of the compounds of the present invention is the "writhing syndrome" test for analgesic activity as described by Seigmund, et al., Proc. Soc, Exp. Biol. and Med., 95:729 (1957) with modifications. Representative compounds of the present invention which are active when tested by the "writhing syndrome" test are: 2-(3-Amino-2-pyrazolin-1-yl)benzothiazole 2-(3-Amino-5-methyl-2-pyrazolin-1-yl)benzothiazole Representative compounds of the present invention have been proven active in vitro as antibacterial and/or antifungal agents when tested by such procedures as the standard agar dilution procedure. Compounds found to be active in these tests are:

2-(3-Amino-2-pyrazolin-1-yl)benzothiazole
2-(3-Amino-4-methyl-2-pyrazolin-1-yl)benzothiazole
2-(3-Amino-5-methyl-2-pyrazolin-1-yl)benzothiazole
2-]3-Amino-5-(p-chlorophenyl)-2-pyrazolin-1-yl]benzothiazole
2-(3-amino-2-pyrazolin-1-yl)pyridine
2-(3-amino-2-pyrazolin-1-yl)-6-chlorpyridine
3-amino-1-(5-chloro-2-pyridyl)-2-pyrazoline
2-(3-amino-4-methyl-2-pyrazolin-1-yl)-6-chloropyridine
2-(3-amino-4-methyl-2-pyrazolin-1-yl)-5-chloropyridine
2-(3-amino-5-methyl-2-pyrazolin-1-yl)pyridine
2-(3-amino-5-methyl-2-pyrazolin-1-yl)-6-chloropyridine
2-(3-amino-5-methyl-2-pyrazolin-1-yl)-5-chloropyridine
2-(3-amino-5-methyl-2-pyrazolin-1-yl)-6-chloropyrazine
2-(3-amino-5-ethyl-2-pyrazolin-1-yl)-6-chloropyridine 2-[3-amino-5-(p-chlorophenyl)-2-pyrazolin-1-yl]-6-chloropyridine 2-(3-amino-5-phenyl-2-pyrazolin-1-yl)-6-chloropyridine.

Adjuvant induced experimental polyarthritis is a specific systemic disease of the rat which shares interesting similarities with rheumatoid arthritis. Specifically, the histology of the two diseases bears a remarkable resemblance as shown by C. M. Pearson et al., Am. J. Path., 42: 73 (1963). E. M. Glenn, Am. J. Vet. Res., 27 (116): 339 (1966) has classified adjuvant induced polyarthritis as a crippling and permanent deformity resulting from diffuse connective tissue involvement around certain susceptible joints in the rat. Zahiri et al., Can. Med. Ass. J., 101: 269 (1969) have shown that the fusiform swelling of the distal joints is associated with edema, congestion and synovitis including pannus formation, all of which precede the ultimate destruction of bone and cartilage. Furthermore, Zahiri et al. indicate that the cartilage destruction in the joint is due to an invasive pannus which originates in the marginal synovium and extends across the articular surface to erode it. When nonsteroidal, anti-inflammatory agents such as indomethacin inhibit arthritic paw swelling, which is composed of inflammatory cell infiltrates, they have also been shown to prevent joint and bone deterioration [see S. Wong et al., J. Pharm. & Exp. Ther., 185: 127 (1973) and G. R. Bobalick et al., Agents and Actions, 4: 364 (1974)]. The most pertinent reference showing the relationship between arthritis and joint deterioration is an X-ray analysis of adjuvant arthritis in the rat by Blackham et al., Agents and Actions, 7: 145 (1977). In a similar manner, inhibition of the progress of arthritis in paws of rats treated with the following compounds of this invention also would lessen associated joint deterioration:

2-(3-Amino-2-pyrazolin-1-yl)-6-chloropyridine
2-(3-Amino-5-methyl-2-pyrazolin-1-yl)-6-chloropyridine The test for showing that compounds of this invention prevent the onset of asthmatic symptoms and allergic diseases in mammals in an effective dose uses the procedure of Lichtenstein, L. M. and Osler, A. G., J. Exp. Med., 120: 507–530 (1964), which evaluates the ability of compounds to inhibit mediator (histamine) release from immunologically stimulated human basophils.

Reagents

10X Concentrated Tris Buffer

Dissolve 140.3 g. of sodium chloride, 7.45 g. of potassium chloride and 74.5 g. of Trizma-Tris Pre-Set, Reagent Grade, pH 7.6, at 25° C. (Sigma Chemical Co.) in sufficient water to give a final volume of 2 liters.

Human albumin (Sigma Chemical Co.) (30 mg./ml.)

Calcium and Magnesium Stocks

Made to 0.075M and 0.5M. respectively, with calcium chloride dihydrate and magnesium chloride hexahydrate.

Tris-A Buffer

A 10 ml. portion of 10X Tris Buffer and 1.0 ml. of human albumin are diluted to 100 ml. with water.

Tris ACM Buffer

A 10 ml. portion of 10X Tris Buffer, 1.0 ml. of human albumin. 0.8 ml. of calcium stock and 0.2 ml. of magnesium stock are diluted to 100 ml. with water.

Rabbit Antihuman IgE

Behring Diagnostics (Generally used at 10 $\mu$g. protein/ml. final concentration.)

House Dust Mite Extract (*Dermatophagoides Farinae*)

Strength 1:100 (w:v) allergenic extract, Hollister-Stier Labs. Generally this is diluted 1:1000 to 1:10,000 (considering the vial as stock).

Other Allergens

Intradermal solutions or intramuscular preparations for hyposensitization, Hollister-Stier Labs. The final concentration used is on the order of 1 PNU/ml.

Separation of Leukocytes from Human Blood and Challenge

Eighty milliliters of blood is withdrawn from subjects with known histamine release to anti-IgE, ragweed antigen or other specific allergen, using four 20 ml. heparinized tubes. This 80 ml. of blood is mixed with 20 ml. of saline containing 0.6 g. of dextrose and 1.2 g. of dextran. The blood is allowed to sediment at room temperature in two 50 ml. polycarbonate centrifuge tubes until a sharp interface develops between the red cells and plasma (60–90 minutes). The plasma (top) layer from each tube is withdrawn by pipet and transferred to respective 50 ml. polycarbonate tubes. The plasma is centrifuged for 8 minutes at 110X g at 40° C. The supernatant is carefully poured off as completely as possible and the cell button is resuspended in 2–3 ml. of Tris-A buffer using a siliconized Pasteur pipet. The resuspension is accomplished by drawing the liquid gently in and out of the pipet, with the tip below the liquid, until an even suspension of cells is obtained. Sufficient Tris-A buffer is then added to bring the volume in the tube to about 45 ml. and the tube is centrifuged at 110X g for 8 minutes at 40° C. The supernatant is poured off and the cell button is resuspended and centrifuged as described above. The supernatant is poured off and the cell button is suspended in 2–3 ml. of Tris-ACM buffer and transferred to a siliconized or polycarbonate vessel with enough Tris-ACM buffer to make the final volume sufficient to allow addition to the reaction tubes.

Reaction tubes containing anti-IgE or antigens, either alone or with test compound in a total volume of 0.2 ml. are prepared and placed in a 37° C. bath. The cells are warmed to 37° C. and frequently swirled to ensure an even suspension, while 1.0 ml. aliquots are added to each reaction tube. The tubes are then incubated for 60 minutes at 37° C., vortexing the tubes gently every 15 minutes to keep the cells evenly suspended. When the reaction is complete, the tubes are centrifuged at 4° C. for 10 minutes at 1500 rpm. to sediment the cells. One ml. aliquots of supernatant are transferred to 12X 75 mm. polyethylene tubes and 0.2 ml. of 8% perchloric acid is added to each tube. Blanks and totals are included in each test. The blanks have cells and all reagents except antigen or anti-IgE. The totals contain 0.24 ml. of 8% perchloric acid, 1 ml. of cells and 0.2 ml. of buffer. All samples are then centrifuged to remove the precipitate protein.

Assay of Released Histamine by the Automated Fluorometric Method

This automated method has been described by Siraganian, R. P., in Anal. Biochem., 57: 383 (1974) and J. Immunol. Methods, 7: 283 (1975) and is based on the manual method of Shore, P. A., et al., J. Pharmacol. Exp. Ther., 217: 182 (1959).

The automated system consists of the following Technicon Autoanalyzer II components: Sampler IV, Dual-Speed Proportioning Pump III, Fluoronephelometer with a narrow pass primary filter 7-60 and a secondary filter 3-74, Recorder, and Digital Printer. The manifold used is the one described by Siraganian vide supra, with the following modifications: the dialyzer is omitted; all pumping tubes pass through a single proportioning pump with large capacity and twice the volume of sample is taken for analysis.

The automated chemistry consists of the following steps: extraction from alkaline saline into butanol, back extraction into dilute hydrochloric acid by addition of heptane, reaction of histamine with o-phtaldialdehyde (OPT) at high pH and conversion of the OPT adduct to a stable fluorophore with phosphoric acid. The reaction product is then passed through the fluorometer. The full scale response is adjusted to 50 ng. histamine base with a threshold sensitivity of approximately 0.5 ng.

Calculation of the Results of Histamine Release Tests

The instrument blank (wash) is subtracted from the ng. histamine of each sample. Then the ng. histamine of each sample is divided by the mean of the three totals (cells lysed with perchloric acid) to obtain percent release.

Control samples contain antigen but no test compound. Blank (or spontaneous release) samples contain neither antigen nor test compound. The mean of the blanks (three replicates) is subtracted from the percent release for controls and test compounds.

The means for control and test compound groups are computed and the result for a test compound is computed as percent of control by the formula:

$$100 \times \frac{\% \text{ Histamine Release with Test Compound}}{\% \text{ Histamine Release in Controls}}$$

Values obtained at different concentrations of test compound are used to calculate an ED50 (the concentration in $\mu M$ which causes a 50% inhibition of histamine release) by linear regression.

The following representative compound would be shown by this procedure to prevent the onset of asthmatic symptoms and allergic diseases in mammals:
2-(3-Amino-5-phenyl-2-pyrazolin-1-yl)-5-chloropyridine Another test for showing that compounds of this invention prevent the onset of asthmatic symptoms in the Lipoxygenase Inhibitor Screening Assay 009. Human platelets are suspended in a physiological buffer incubated for 20 minutes with 200 $\mu M$ of arachidonic acid at 37° C. in the presence of a vehicle or test compound. Incubation is terminated by methanol addition. Measurement of the lipoxygenase product 12-hydroxyeicosatetraenoic acid by high performance liquid chromatography is the measure of lipoxygenase activity. The most potent mediators of the asthmatic bronchospasm are the leukotrienes C, D and E. These mediators are derived from the lipoxygenation of arachidonate. Therefore, inhibitors derived from this assay are expected to inhibit the broncho-spasm and be useful in effective asthma therapy. Such exemplary compounds would include the following:

2-(3-Amino-5-methyl-2-pyrazolin-1-yl)-6-chloropyrazine
2-[3-Amino-5-(p-chlorophenyl)-2-pyrazolin-1-yl]-6-chloro-pyridine
2-[3-Amino-5-(p-chlorophenyl)-2-pyrazolin-1-yl]-benzothiazole The compounds of the present invention have been found to be highly useful for the above pharmaceutical therapy, when administered in amounts ranging from about 0.5 milligram to about 250 mg. per kilogram of body weight per day. A preferred dosage regimen for optimum results would be from about 5 mg. to about 100 mg. per kilogram of body weight per day, and such dosage units are employed that a total of from about 0.35 gram to about 7.0 grams of the active ingredient for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active ingredient may be administered in any convenient manner such as by the oral, intravenous, intramuscular, intra-articular, topical or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are for example, myristyl-gamma-picolinium chloride, phenyl mercuric nitrate, benzalkonium chloride, phenethyl alcohol, p-chlorophenyl-α-glycerol ether, methyl and propyl parabens, and thimerosal. As a practical matter it is also convenient to employ antioxidants. Suitable antioxidants include, for example, sodium bisulfite, sodium metabisulfite and sodium formaldehyde sulfoxylate. Generally, from about 0.05 to about 0.2% concentrations of antioxidant are employed.

For intramuscular injection, the preferred concentration of active compound is 0.25 to 0.50 mg./ml. of the finished compositions. The compounds of this invention are equally adapted to intravenous administration when diluted with water or diluents employed in intravenous therapy such as isotonic glucose in appropriate quantities. For intravenous use, initial concentrations down to about 0.05 to 0.25 mg./ml. of active compound are satisfactory.

The active compounds of the present invention may be orally administered, for example, with an inert diluent or with an assimilable edible carrier. They may be enclosed in hard or soft shell gelatin capsules or compressed into tablets. Also they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active ingredient in such therapeutically useful compositions is such that a suitable dosage will be obtained. Preferred compositions or preparations according to the present invention are prepared so that an oral dosage unit form contains between about 50 and 250 milligrams of active compound.

The tablets, troches, pills, capsules and the like may also contain the following: a binder such as gum tragacanth, acacia, corn starch or gelatin, excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives a dye and flavoring such as cherry or orange flavor. Of course, any material used in preparing any dosage unit form should be pharmaceutically pure and substantially nontoxic in the amounts employed.

For the control of asthma or allergic responses, the active ingredient may also be administered by inhalation. For the inhalation routes, an inhaler device may be employed with the active ingredient in a suitable form such as powder or solution with appropriate pharmaceutical carriers.

A further understanding of the invention can be obtained from the following non-limiting examples.

EXAMPLE 1

2-(3-Amino-2-pyrazolin-1-yl)pyridine

A 0.58 g. amount of sodium metal is dissolved in 150 ml. of absolute ethanol, then 14.0 g. of 2-hydrazinopyridine is added followed by 12.7 g. of betaethoxypropionitrile. The reaction mixture is refluxed on a steam bath for 16 hours, then the solvent is removed in vacuo. Water is added and the solid collected by filtration. The solid is recrystallized twice from acetone to give 5.55 g. of the product of the Example as tan colored crystals, m.p. 168.5°–171° C.

EXAMPLE 2

2-(3-Amino-2-pyrazolin-1-yl)-6-chloropyridine

A mixture of 100 g. of 2,6-dichloropyridine in 200 ml. of hydrazine hydrate is stirred and refluxed for 5 hours. The reaction mixture is cooled and filtered. The product is washed with water and dried to give 47.7 g. of 2-chloro-6-hydrazinopyridine, m.p. 117°–119° C.

A 0.32 g. amount of sodium metal is dissolved in 100 ml. of absolute ethanol, then 10.0 g. of the product of Example 1 is added, followed by 4.0 g. of acrylonitrile. The reaction mixture is refluxed for 18 hours. The solvent is removed in vacuo and water is added to the residue to separate a solid. The solid is collected by filtration, dissolved in dichloromethane, dried over magnesium sulfate, filtered through magnesium silicate and concentrated while adding hexane, to separate crystals. The mixture is cooled and filtered to give 9.3 g. of the product of the Example as a pale yellow solid, m.p. 143°–145° C.

EXAMPLE 3

3-Amino-1-(5-chloro-2-pyridyl)-2-pyrazoline

A mixture of 16.1 g. of 2,5-dichloropyridine in 32 ml. of hydrazine hydrate is stirred and refluxed for 15 hours. The reaction mixture is cooled and water is added. The precipitate is collected by filtration, washed with water and dried to give 12.7 g. of 5-chloro-2-hydrazinopyridine as a white solid, m.p. 127°–128° C.

A 0.08 g. amount of sodium metal is dissolved in 10 ml. of absolute ethanol, then 2.5 g. of 5-chloro-2-hydrazinopyridine is added, followed by 1.70 g. of betaethoxypropionitrile. The procedure of Example 1 is continued to give 1.40 g. of the product of the Example as yellow crystals, m.p. 203°–204.5° C.

EXAMPLE 4

2-(3-Amino-4-methyl-2-pyrazolin-1-yl)-6-chloropyridine

As for Example 2 a 0.32 g. amount of sodium metal is dissolved in 100 ml. of absolute ethanol, then 10.0 g. of 2-chloro-6-hydrazinopyridine is added, followed by 4.8 g. of methacrylonitrile in place of acrylonitrile. The procedure of Example 2 is followed to give 9.4 g. of crude product. The material is recrystallized from dichloromethane-hexane to give the product of the Example as pale yellow crystals, m.p. 175°–176° C.

EXAMPLE 5

2-(3-Amino-4-methyl-2-pyrazolin-1-yl)-5-chloropyridine

As for Example 4 a 0.2 g. amount of sodium metal is dissolved in 50 ml. of absolute ethanol, then 5.0 g. of 5-chloro-2-hydrazinopyridine (Example 3) is added, followed by 4.8 g. of methacrylonitrile. The reaction mixture is refluxed for 18 hours. The solvent is removed in vacuo and water is added to give a gum which solidifies. The solid is collected by filtration, and washed with water. The solid is dissolved in dichloromethane, dried over magnesium sulfate and filtered through anhydrous magnesium silicate. The filtrate is evaporated and the residue is triturated with hexane to give a brown solid. The solid is dissolved in dichloromethane and hexane is added while concentrating to separate a solid. The mixture is cooled and filtered to give 3.4 g. of a gray solid. The desired product is recrystallized from dichloromethane-hexane to give a white solid, m.p. 159°–160° C.

EXAMPLE 6

2-(3-Amino-5-methyl-2-pyrazolin-1-yl)pyridine

A 0.3 g. amount of sodium metal is dissolved in 100 ml. of absolute ethanol, then 5.45 g. of 2-hydrazinopyridine is added, followed by 3.35 g. of crotononitrile (mixture of cis or trans isomers). The reaction mixture is refluxed for 3 hours, then the solvent is removed in vacuo. Water is added and the solid is collected by filtration. The solid is recrystallized from dichloromethane-hexane, then acetone-hexane to give 3.1 g. of the product of the Example as yellow crystals, m.p. 154°–157° C.

EXAMPLE 7

2-(3-Amino-5-methyl-2-pyrazoline-1-yl)-6-chloropyridine

A 0.23 g. amount of sodium metal is dissolved in 75 ml. of absolute ethanol, then 7.2 g of 2-chloro-6-hydrazinopyridine is added followed by 3.4 g. of distilled crotononitrile. The reaction mixture is refluxed for 18 hours and the procedure of Example 5 is followed through the anhydrous magnesium silicate filtration step. The filtrate is evaporated to give a dark orange gum which crystallizes on standing. The residue is dissolved in ether, treated with activated charcoal and filtered through diatomaceous earth. The filtrate is concentrated while adding hexane at reflux to yield an oil. The oil is seeded and cooled. Ether is added and continued cooling provides light yellow crystals. The mixture is filtered to give 5.2 g. of the desired product as pale yellow crystals, m.p. 105°–107° C.

EXAMPLE 8

2-(3-Amino-5-methyl-2-pyrazolin-1-yl)-5-chloropyridine

A mixture of 0.20 g. of sodium metal dissolved in 50 ml. of absolute ethanol, 5.0 g. of 3-chloro-6-hydrazinopyridine and 4.8 g. of crotononitrile is heated at reflux for 18 hours. The procedure of Example 5 is followed through the evaporation of the magnesium silicate filtrate to give a yellow gum. Trituration with hexane gives a yellow solid. The solid is dissolved in dichloromethane. This solution is concentrated by heating on a steam bath while adding hexane, then is cooled in a refrigerator to separate 3.3 g. of the product of the Example as pale yellow crystals, m.p. 168°–170° C.

EXAMPLE 9

2-(3-Amino-5-methyl-2-pyrazolin-1-yl)-6-chloropyrazine

A 45 g. amount of 2,6-dichloropyrazine in 150 ml. of warm ethanol is slowly treated with 30 ml. of hydrazine (95+%). The mixture is refluxed for 2 hours, then evaporated in vacuo. The residue is shaken with 200 ml. of water and filtered. The precipitate is washed with water and air dried to give 33.0 g. of crude product. A 7.0 g amount of the above product is recrystallized from 100 ml. of ethanol cooled at −10° C. The solid is collected, washed with ether and dried in vacuo at room temperature to give 2.8 g. of 2-chloro-6-hydrazinopyrazine, m.p. 136°–137° C.

A 0.30 g. amount of sodium metal is dissolved in 100 ml. of absolute ethanol, then 6.72 g. of 2-chloro-6-hydrazinopyrazine (prepared as described above) is added and after 5 minutes, 4.6 g. of distilled crotononitrile is added. The reaction mixture is refluxed for 6 hours. The solvent is removed in vacuo and water is added to the residue to separate a gum. The gum is dissolved in dichloromethane, dried over magnesium sulfate and filtered. The filtrate is evaporated to give a gum. The gum is treated with benzene to separate yellow crystals. The crystals are collected, dried and recrystallized from acetone-hexane to give 1.4 g of the desired product as yellow crystals, m.p. 147°–148° C.

EXAMPLE 10

2-(3-Amino-5-ethyl-2-pyrazolin-1-yl)-6-chloropyridine

A solution of 124 g. of sodium methylate in 414 g. of methanol, diluted with 51 ml. of N,N-dimethylformamide is added via a dropping funnel to a stirred solution of 100 g. of diethylcyanomethylphosphorate and 35 g of freshly distilled propionaldehyde in 75 ml. of N,N-dimethylformamide maintained at 40°–45° C. in an ice bath. After the addition is complete the reaction mixture is warmed to 50° C. and stirring is continued for one hour without further external heating or cooling. The reaction mixture is diluted with 270 ml. of 50:50 methanol-water then the pH of the mixture is adjusted to a pH 7.0 with glacial acetic acid and the neutral solution is extracted thoroughly with ether. The combined ether extracts are washed with dilute acetic acid then, with water. The organic layer is dried over magnesium sulfate, filtered and concentrated in vacuo to an oil. The oil is distilled through a 2 foot saddle-filled column, giving 29.0 g. of 3-methoxyvaleronitrile, b.p. 42° C. at 3 mm., $n_D^{25}$ 1.4190.

A 0.26 g. amount of sodium metal is dissolved in 100 ml. of absolute ethanol, then 8.1 g. of 2-chloro-6-hydrazinopyridine (Example 2) is added followed by 6.4 g. of 3-methoxyvaleronitrile. The reaction mixture is refluxed for 16 hours, then is evaporated in vacuo to give a solid. The solid is dissolved in water/dichloromethane. The organic layer is separated, dried over magnesium sulfate, filtered through anhydrous magnesium silicate and concentrated while adding hexane to yield 7.0 g. of pale yellow crystals. A 200 mg. amount of the crude product is recrystallized from dichloromethanehexane to give 171 mg. of the product of the Example, as pale yellow crystals, m.p. 131°–133° C.

EXAMPLE 11

2-(3-Amino-2-pyrazolin-1-yl)benzothiazole

A mixture of 5.0 g. of β-ethoxypropionitrile, 100 ml. of absolute ethanol, 8.25 g. of 2-hydrazinobenzothiazole and 2.5 g. of 50% w/v choline in methanol is refluxed on a steam bath for 16 hours, then the solvent is removed in vacuo. Water is added and the solid is collected by filtration. The solid is recrystalized twice from ethanol to give 5.75 g. of the product of the Example as grey prisms, m.p. 231.5°–235° C.

EXAMPLE 12

2-(3-Amino-4-methyl-2-pyrazolin-1-yl)benzothiazole

A 0.5 g. amount of sodium metal is dissolved in 100 ml. of absolute ethanol, then 16.5 g. of 2-hydrazinobenzothiazole is added followed by 6.7 g. of methacrylonitrile. The reaction mixture is refluxed for 4 hours, then is cooled. Some of the ethanol is removed in vacuo and the precipitate is collected by filtration to give 20.6 g. of the desired product as colorless prisms, m.p. 207°–209° C.

EXAMPLE 13

2-(3-Amino-5-methyl-2-pyrazolin-1-yl)benzothiazole

A mixture of 20.1 g. of crotononitrile, 80 ml. of absolute ethanol, 4.87 g. of 2-hydrazinobenzothiazole and 1.5 ml. of 50% methanolic choline is refluxed for 16 hours. The solvent is removed in vacuo and water is added. The separated solid is collected by filtration, dissolved in dichloromethane, and passed through a short column of hydrous magnesium silicate. The effluent is refluxed with the gradual addition of hexane to give a crystalline product. The crystallization step is repeated to give 0.5 g. of the product of the Example as off-white plates, m.p. 212°–215° C.

EXAMPLE 14

2-[3-Amino-5-(p-chlorophenyl)-2-pyrazolin-1-yl]benzothiazole

A mixture of 3.28 g. of p-chlorocinnamonitrile, 50 ml. of absolute ethanol, 3.1 g. of 2-hydrazinobenzothiazole and 1.0 g. of 50% w/v choline in methanol is refluxed on a steam bath for 16 hours. The reaction mixture is cooled and the precipitate is collected by filtration. The solid is washed with ethanol to yield 3.2 g. of crude product. This material is recrystallized from acetone to give 1.65 g. of the product of the Example as yellow crystals, m.p. 273°–275° C.

EXAMPLE 15

2-(3-Amino-5-p-tolyl-2-pyrazolin-1-yl)benzothiazole

A 0.50 g. amount of sodium metal is dissolved in 250 ml. of absolute ethanol, then 8.3 g. of 2-hydrazinobenzothiazole is added followed by 7.4 g. of 4-methylcinnamonitrile. The reaction mixture is refluxed for 4 hours then is cooled. The precipitate formed is collected by filtration and washed with ethanol then water to give 13.7 g. of crude product. This material is recrystallized from 2-methoxyethanol, filtered and washed with hexane then methanol to give 8.55 g. of the desired product as colorless prisms, m.p. 282°–285° C.

EXAMPLE 16

2-(3-Amino-5-phenyl-2-pyrazolin-1-yl)benzothiazole

A 0.46 g. amount of sodium metal is dissolved in 150 ml. of absolute ethanol, then 16.5 g. of 2-hydrazinobenzothiazole is added, followed by 12.9 g. of cinnamonitrile. The reaction mixture is refluxed for 16 hours, then is cooled. Some of the solvent is removed in vacuo and the mixture is filtered. The precipitate is washed with hexane to give 25.67 g. of crude product. A 3.0 g. amount of this material is recrystallized from acetone-hexane to give 2.35 g. of the product of the Example as buff colored prisms, m.p. 270°–271.5° C.

EXAMPLE 17

2-(3-Amino-5-phenyl-2-pyrazolin-1-yl)benzothiazole hydrochloride.¼H₂O

A 2.0 g. amount of 2-(3-amino-5-phenyl-2-pyrazolin-1-yl)benzothiazole (Example 6) is dissolved in 20.0 ml. of N,N-dimethylformamide. The solution is acidified with 5N ethanolic hydrochloric acid. The solvent is removed in vacuo and the residue is crystallized from ether-methanol at 5° C. to give 2.0 g. of the product of the Example as green crystals, m.p. 275°–285° C.

EXAMPLE 18

2-(3-Amino-5-phenyl-2-pyrazolin-1-yl)-5-chloropyridine

A 0.5 g. amount of sodium metal is dissolved in 150 ml. of absolute ethanol, then 14.36 g. of 5-chloro-2-hydrazinopyridine (prepared as described in Example 3) is added followed by 12.92 g. of cinnamonitrile. The reaction mixture is refluxed for 16 hours. The solvent is removed in vacuo and water is added to the residue to separate a solid. The solid is collected by filtration and dissolved in dichloromethane. The solution is dried over anhydrous sodium sulfate and filtered through a hydrous magnesium silicate. The filtrate is concentrated while adding hexane to separate crystals. The material is recrystallized from ethyl acetate to give 11.68 g. of a light yellow crystalline material. The material is dried in vacuo to give the product of the Example as yellow crystals, m.p. 142°–147° C.

EXAMPLE 19

2-(3-Amino-4-methyl-2-pyrazolin-1-yl)-6-methylpyridine

A 200 ml. amount of hydrazine hydrate is added to 100 g. of 6-chloro-2-picoline (98%) and the mixture is refluxed for 16 hours.

The excess hydrazine is removed in vacuo and the residual oil is dissolved in dichloromethane and extracted with three 100 ml. portions of water. The organic layer is dried over anhydrous sodium sulfate and evaporated in vacuo to an oil. Evaporation is continued until crystals begin to form then hexane is added to separate a crystalline mass. This material is recrystallized from hexane after treatment with activated charcoal to yield 26.57 g. of 2-hydrazino-6-methylpyridine, m.p. 53°–56° C.

A 0.51 g. amount of sodium metal is dissolved in 150 ml. of absolute ethanol, then 12.32 g. of 2-hydrazino-6-methylpyridine is added, followed by 6.7 g. of methacrylonitrile. The reaction mixture is refluxed on a steam bath for 16 hours then is evaporated in vacuo to an oil. Water is added to separate a solid. The solid is collected and recrystallized from ethyl acetate after treatment with activated charcoal to give 10.12 g. of the desired product as white crystals, m.p. 181°–185° C.

EXAMPLE 20

2-(3-Amino-4-methyl-2-pyrazolin-1-yl)pyridine

A 1.02 g. amount of sodium metal is dissolved in 250 ml. of absolute ethanol, then 21.8 g. of 2-hydrazinopyridine is added, followed by 13.4 g. of methacrylonitrile. The reaction mixture is refluxed for 16 hours, then the solvent is removed in vacuo. The solid is recrystallized twice from 3A ethanol after treatment with activated charcoal to give 4.30 g. of a tan solid. The above recrystallization filtrates are combined and evaporated in vacuo to a solid. The solid is dissolved in dichloromethane and passed through a hydrous magnesium silicate. The filtrate is concentrated while adding hexane at reflux to crystallize an additional 16.4 g. of the desired product (total 20.79 g.) as tan crystals, m.p. 149°–151° C.

EXAMPLE 21

2-(3-Amino-5-phenyl-2-pyrazolin-1-yl)pyridine

A 1.02 g. amount of sodium metal is dissolved in 250 ml. of absolute ethanol, then 21.82 g. of 2-hydrazinopyridine is added, followed by 25.8 g. of cinnamonitrile. The reaction mixture is refluxed for 16 hours, then the solvent is removed in vacuo. Water is added and the solid is collected by filtration. The solid is recrystallized from 3A ethanol to yield 20.32 g. of the desired product as yellow crystals, m.p. 203°–206° C.

EXAMPLES 22 TO 33

Following substantially the procedure set out in Example 2 the various hydrazino compounds is condensed with acrylonitrile to produce the corresponding Example title compound.

| Example | Example Title Compound | Hydrazine |
|---|---|---|
| Example 22 | 2-(3-amino-2-pyrazolin-1-yl)-3,5-dichloropyridine | 3,5-dichloro-2-hydrazinopyridine |
| Example 23 | 2-(3-amino-2-pyrazolin-1-yl)-3-methylquinoxaline | 2-hydrazino-3-methylquinoxaline |
| Example 24 | 2-(3-amino-2-pyrazolin-1-yl)-4,6-dimethyl-s-triazine | 2-hydrazino-4,6-dimethyl-s-triazine |
| Example 25 | 2-(3-amino-2-pyrazolin-1-yl)-benzoxoazole | 2-hydrazino-benzoxoazole |
| Example 26 | 2-(3-amino-2-pyrazolin-1-yl)-5-chloro-3-nitropyridine | 5-chloro-2-hydrazino-3-nitropyridine |
| Example 27 | 1-(3-amino-2-pyrazolin-1-yl)-isoquinoline | 1-hydrazinoisoquinoline |
| Example 28 | 6-(3-amino-2-pyrazolin-1-yl)-purine | 6-hydrazinopurine |
| Example 29 | 2-(3-amino-2-pyrazolin-1-yl)-4,6-dimethylpyrimidine | 2-hydrazino-4,6-dimethylpyrimidine |
| Example 30 | 2-(3-amino-2-pyrazolin-1-yl)-3-chloropyridine | 3-chloro-2-hydrazinopyridine |
| Example 31 | 2-(3-amino-2-pyrazolin-1-yl)-6-bromopyridine | 2-bromo-6-hydrazinopyridine |
| Example 32 | 2-(3-amino-2-pyrazolin-1-yl)-6-methoxypyridine | 2-hydrazino-6-methoxypyridine |
| Example 33 | 2-(3-amino-2-pyrazolin-1-yl)-2-thiazoline | 2-hydrazino-thiazole |

EXAMPLE 34

| Preparation of Compressed Tablet | |
|---|---|
| Ingredient | mg./tablet |
| Active Compound | 0.5–500 |
| Dibasic Calcium Phosphate N.F. | qs |
| Starch USP | 40 |
| Modified Starch | 10 |
| *Surfactant, e.g. Sodium Lauryl Sulfate | 0.1–2.0 (% w/w) |
| Magnesium Stearate USP | 0.1–5.0 (% w/w) |

*Other surface active agents such as disodium sulfosuccinate and nonionic surface active agents may also be employed.

EXAMPLE 35

| Preparation of Compressed Tablet | |
|---|---|
| Ingredient | mg./tablet |
| Active Compound | 0.5–500 |
| Direct Compression Sugar Agent | qs |
| Magnesium Stearate | 0.1–3.0 (% w/w) |

EXAMPLE 36

| Preparation of Hard Shell Capsule | |
|---|---|
| Ingredient | mg./capsule |
| Active Compound | 0.5–500 |
| Lactose, Spray Dried | qs |
| Magnesium Stearate | 0.1–3.0 (% w/w) |

EXAMPLE 37

| Preparation of Oral Liquid (Syrup) | |
|---|---|
| Ingredient | % w/v |
| Active Compound | 0.05–5 |
| Liquid Sugar | 75.0 |
| Methyl Paraben USP | 0.18 |
| Propyl Paraben USP | 0.02 |
| Suspending Agent | 0.5–1.0 |
| Flavoring Agent | qs |
| Purified Water qs ad | 100.0 |

EXAMPLE 38

| Preparation of Oral Liquid (Elixir) | |
|---|---|
| Ingredient | % w/v |
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 39

| Preparation of Oral Suspension (Syrup) | |
|---|---|
| Ingredient | % w/v |
| Active Compound | 0.05–5 |
| Polysorbate 80 USP | 0.1 |
| Magnesium Aluminum Silicate, Colloidal | 0.3 |
| Dye | 0.001–0.5 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 40

| Preparation of Injectable Solution | |
|---|---|
| Ingredient | % w/v |
| Active Compound | 0.05–5 |
| Benzyl Alcohol N.F. | 0.9 |
| Water for Injection | 100.0 |

EXAMPLE 41

| Preparation of Injectable Oil | |
|---|---|
| Ingredient | % w/v |
| Active Compound | 0.05–5 |
| Benzyl Alcohol | 1.5 |
| Sesame Oil qs ad | 100.0 |

EXAMPLE 42

| Preparation of Intra-articular Product | |
|---|---|
| Ingredient | Amount |
| Active Compound | 2–20 mg. |
| NaCl (physiological saline) | 0.9% |
| Benzyl Alcohol | 0.9% |
| Sodium Carboxymethylcellulose | 1–5% |
| pH adjusted to 5.0–7.5 | |
| Water for Injection qs ad | 100% |

EXAMPLE 43

| Preparation of Injectable Depo Suspension | |
|---|---|
| Ingredient | % w/v |
| Active Compound | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6–8 | qs |
| Water for Injection qs ad | 100.0 |

EXAMPLE 44

| Preparation of Topical Cream | |
|---|---|
| Ingredient | % w/w |
| Active Compound | 0.05–5 |
| Sodium Lauryl Sulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |

| Preparation of Topical Cream | |
|---|---|
| Ingredient | % w/w |
| Purified Water qs | 100 |

EXAMPLE 45

| Preparation of Topical Ointment | |
|---|---|
| Ingredient | % w/w |
| Active Compound | 0.05–5 |
| Cholesterol | 3 |
| Stearyl Alcohol | 3 |
| White Wax | 8 |
| Petrolatum, White USP qs | 100 |

EXAMPLE 46

2-[3-Amino-5-(p-chlorophenyl)-2-pyrazolin-1-yl]-6-chloropyridine

An 0.3 g. amount of sodium metal is dissolved in 100 ml. of absolute ethanol, then 7.2 g. of 2-chloro-6-hydrazinopyridine (Example 2) is added, followed by 8.2 g. of 4-chlorocinnamonitrile. The reaction mixture is refluxed for 18 hours, then is evaporated in vacuo to a gum. Water is added to give a solid. The solid is collected and dissolved in dichloromethane, dried over magnesium sulfate and filtered. The filtrate is concentrated while adding hexane to separate yellow crystals on cooling. The product is collected and washed with ether-hexane to give 10.3 g. of tan solid. The solid is dissolved in dichloromethane, filtered through absorbent magnesium silicate, then is concentrated while adding hexane to give the product of the Example as white crystals, m.p. 157°–158°.

EXAMPLE 47

2-(3-Amino-5-phenyl-2-pyrazolin-1-yl)-6-chloropyridine

As for Example 2, a mixture of 0.23 g. of sodium metal, 50 ml. of absolute ethanol, 7.11 g. of 2-chloro-6-hydrazinopyridine and 6.5 g. of cinnamonitrile yields 7.35 g. of crude product. The crude material is dissolved in dichloromethane, filtered through hydrous magnesium silicate and concentrated while adding hexane to give 5.90 g. of the desired product as off-white crystals, m.p. 187.5°–188.5° C.

We claim:

1. A compound which is 2-(3-amino-5-methyl-2-pyrazolin-1-yl)-6-chloropyrazine.

* * * * *